United States Patent [19]

Grose

[11] 4,182,345
[45] Jan. 8, 1980

[54] BODY IMPLANTABLE SIGNAL GENERATOR ASSEMBLY

[75] Inventor: Gary M. Grose, Brooklyn Park, Minn.

[73] Assignee: Medtronic, Inc., Minneapolis, Minn.

[21] Appl. No.: 894,359

[22] Filed: Apr. 7, 1978

[51] Int. Cl.² .............................................. A61N 1/36
[52] U.S. Cl. ................................................ 128/419 P
[58] Field of Search ........ 128/419 P, 419 PG, 419 PS

[56] References Cited

U.S. PATENT DOCUMENTS

| | | | |
|---|---|---|---|
| 3,683,932 | 8/1972 | Cole | 128/419 P |
| 3,760,332 | 9/1973 | Berkovits et al. | 128/419 P |

*Primary Examiner*—William E. Kamm

*Attorney, Agent, or Firm*—Lindquist & Vennum

[57] ABSTRACT

A signal generator assembly having a signal generator and a preformed connector mechanically secured to each other. Posts extend from the signal generator into apertures in the connector. Orifices in the connector intersect the apertures and means are provided to engage the posts within the apertures through the orifices. In a preferred embodiment, the posts are provided with keyways and keys are inserted through the orifices to engage the keyways. The keys may be formed as wedges, preferably having a locking taper, to urge the connector and signal generator into firmer contact. A resilient cushion may be provided between the connector and the signal generator to enhance the interaction of the components.

9 Claims, 4 Drawing Figures

U.S. Patent   Jan. 8, 1980   4,182,345
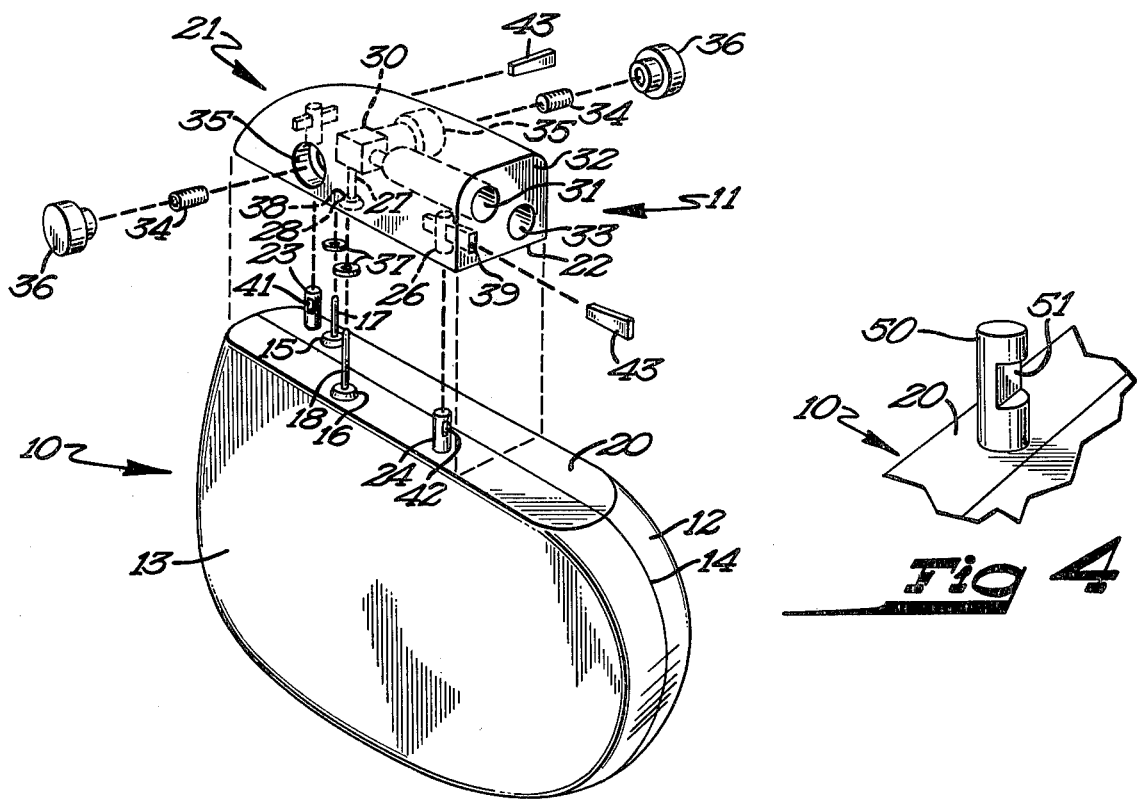
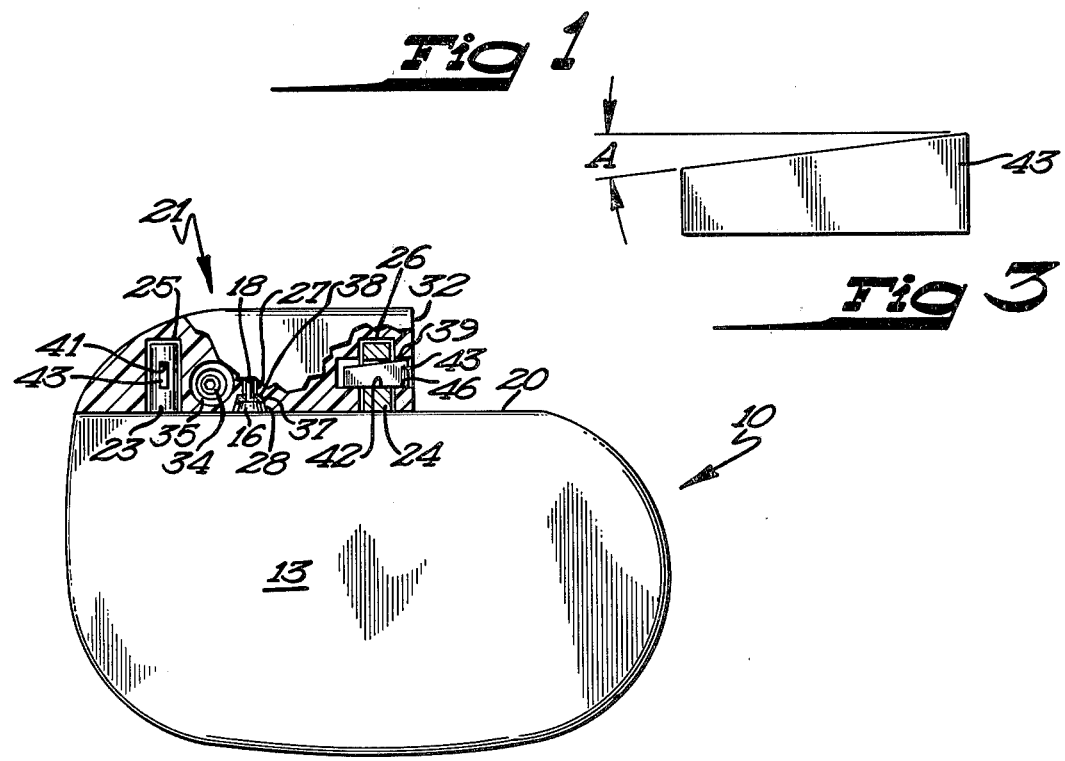

BODY IMPLANTABLE SIGNAL GENERATOR ASSEMBLY

BACKGROUND OF THE INVENTION

Body implantable stimulators are known to the prior art, the most common being the cardiac pacemaker. Typically, such stimulators are formed of a separable lead and signal generator assembly with provision being made to electrically and mechanically interconnect the lead and generator to complete the stimulator unit.

Many prior art signal generators have been formed by molding the components, including mechanical and electrical connections for the lead, in a matrix of encapsulating material which supports the components and shields them from the body environment. Typically, the encapsulating material is an epoxy.

In the body environment it is generally recognized that an enclosed and hermetically sealed signal generator is more reliable as a result of the known and controlled environment provided by the hermetic seal. For this reason, many recent signal generator designs include a rigid enclosure formed of a plurality of preformed members which may be welded together to complete the enclosure. The interconnection between the generator and the lead, when it is desired that these members be separable, occurs outside of the enclosure. While it is common to mold an interconnect assembly from epoxy, such a process diminishes a benefit of a preformed enclosure—elimination of the epoxy encapsulation process. Thus a preformed interconnect assembly, which may be reliably secured to a preformed enclosure housing the generator components, would greatly facilitate assembly of the stimulator. The amount of handling would be reduced with the remaining handling being easier to perform than an epoxy molding process.

A preformed interconnect assembly is disclosed in application Ser. No. 793,642, filed May 4, 1977 in the name of Richard A. Jones, which application is commonly owned with the present invention. The interconnect assembly of the referenced application eliminates the necessity of forming that assembly in place, as by an epoxy molding process, for example. However, that preformed assembly still requires the use of epoxy, or a similar substance, to adhere it to the signal generator enclosure. Additionally, the electrical connection between the interconnect assembly terminal and the signal generator requires manipulation of a wire to position it and a weld, or other process, to secure it in position. Thus, while the interconnect assembly of the referenced application greatly reduces the handling necessary to form and position an interconnect assembly on a signal generator unit, considerable handling remains necessary.

An improvement over the above referenced interconnect assembly is disclosed in application Ser. No. 894,358, filed Apr. 7, 1978, in the name of Lyle A. Ware, which application is commonly owned with the present invention. The invention of the second referenced application provides a preformed interconnect assembly or connector which may be mechanically secured to a signal generator thereby eliminating the need to use epoxy, or a similar substance, to secure the connector to the generator. A hook and a threaded stud extend from a platform on the signal generator. The hook engages an aperture in the preformed connector while the threaded stud extends through a second aperture wherein it is engaged by a nut. Electrical communication with the signal generator components is via upstanding feed-through connections which engage terminals carried within the connector. The signal generator assembly is assembled by first engaging the hook within its aperture, aligning the feed-through connections with apertures which extend to the connector terminals, and pivoting the connector about the hook to insert the stud and feed-through connections within their associated apertures. On tighting of the nut, the connector is firmly secured to the signal generator unit. However, the pivotable motion necessary on assembly provides a cumbersome alignment between the feed-through connections and their associated apertures. Additionally, the threaded stud and nut arrangement may be easily tampered with, without detection.

SUMMARY OF THE INVENTION

The present invention provides an improved mechanical interconnection between a preformed connector and signal generator. Posts extend from a platform on the signal generator in the same general direction as the feed-through connections. Apertures within the connector accept the posts. Thus, the connector may be positioned on the signal generator by a "straight line" motion as opposed to the pivotable motion discussed above. Orifices in the connector intersect the apertures and means are provided to engage the posts within the apertures through the orifices to secure the connector in position on the signal generator. In a preferred embodiment, the posts are provided with keyways and keys are inserted through the orifices to engage the keyways. The keys may be formed as wedges, preferably having a locking taper, to urge the connector and signal generator into firmer contact. The wedge connection disclosed herein is more difficult to remove than a nut connection thereby rendering the completed assembly less susceptible to tampering. Additionally, this connection system requires a minimum amount of space and allows inexpensive tolerances and assembly tooling. A resilient cushion may be provided between the connector and signal generator to enhance the interaction of the components.

BRIEF DESCRIPTION OF THE DRAWINGS

FIG. 1 is an exploded view illustrating a preferred embodiment of the present invention.

FIG. 2 is partial cutaway and cross section further illustrating the embodiment of FIG. 1.

FIG. 3 illustrates a portion of the embodiment of FIGS. 1 and 2.

FIG. 4 illustrates an alternative configuration of a portion of the embodiment of FIGS. 1 and 2.

DETAILED DESCRIPTION OF THE DRAWINGS

Referring now to FIG. 1, there shown an exploded view of a signal generator assembly including a signal generator indicated generally at 10 and a connector indicated generally at 11. Signal generator 10 includes all the necessary signal generating components and power sources within an enclosure formed by two body members 12 and 13 joined together at a seam 14 in known matter, as by welding, for example. Electrical feed-throughs 15 and 16 provide electrical communication with the enclosed components, in known manner, the feed-throughs having electrical connections 17 and 18. The feed-throughs 15 and 16 extend from a platform 20 which is adapted to receive the connector 11 in a manner to be described more fully below.

The connector 11 includes a body portion 21 which may be formed in any known manner, as by molding, for example. Preferably, the body 21 is of a clear material so as to allow visual verification of the electrical connections. The body 21 may be formed of many known materials, including polysolfone as sold under the trademark UDEL by Union Carbide, polyurethane as sold under the trademark PELLATHANE by Upjohn, polymethylpentene as sold under the trademark TPX by Mitsui and others.

The undersurface 22 of the body 21 is adapted to rest on the platform 20 of the signal generator 10 while the outer surface 27 is configured so as to extend the general outer configuration of the signal generator 10 when the surfaces 20 and 22 are mated. Extending from the platform 20 are studs or posts 23 and 24. Apertures 25 and 26 extend from the undersurface 22 of body 21 and are positioned and configured to accept the studs 23 and 24. Apertures 27 (one shown) extend from the undersurfaces 22 of body 21 to accept feed-through connections 17 and 18, the apertures 27 having an enlarged portion 28 to accommodate feed-throughs 15 and 16. For the purpose of clarity, only one aperture 27 is illustrated although a similar aperture is to be provided for each feed-through connection. Apertures 27 extend between the undersurface 22 of body 21 and terminals 30 (one shown) carried within the body 21, the terminals being adapted to establish electrical communication between feed-through connections 17 and 18 and pin-type leads inserted through apertures 31 and 33. Electrical contact between the feed-through connections 17 and 18 and the pin connections of the leads inserted through the apertures 31 and 33 may be made in any desirable manner, it being known to engage a pin-type lead within a terminal such as 30 via set screws 34. Access to set screws 34 is obtained via apertures 35 in the body 21, the apertures 35 being closed by grommets 36, all in known manner.

The feed-through connections 17 and 18 and the posts 23 and 24 extend from the platform 20 of signal generator 10 in the same general direction. Similarly, the apertures 25, 26 and 27 for the posts 23, 24 and feed-through connections 17 and 18 (only one aperture 27 being illustrated) extend from the undersurface 22 of body 21 in the same general direction and are positioned to receive their associated extending member when the body 21 is aligned over the platform 20. Movement of the body 21 toward the platform 20 in a "straight line" motion (generally perpendicular to the platform 20) causes the posts 23 and 24 and feed-through connections 17 and 18 to enter their associated aperture allowing the undersurface 22 of body 21 to rest on the platform 20 of signal generator 10. Resilient washers 37 may be provided to surround the feed-through connections 17 and 18 to rest atop the feed-throughs 15 and 16. The shoulder 38 formed at the junction of the apertures 27 and 28 will engage the resilient washers 37 when the undersurface 22 of the body 21 and platform 20 of signal generator 10 are in close proximity and compress the washers 37 thereby providing a seal to isolate the feed-through connectors 17 and 18 from the body environment. The resilient washers 37 provide an additional function with respect to the mechanical interconnection, in a manner to be described more fully below.

An orifice 39 extends from face 32 of body 21 to intersect the aperture 26. Similarly, an orifice 40 extends from surface 27 to intersect the aperture 25. Keyways 41 and 42 are provided in posts 23 and 24, respectively, the keyways 41 and 42 being in alignment with the orifices 40 and 39, respectively, when the undersurface 22 of body 21 is in proximity to the platform 20 of signal generator 10. Keys 43 are insertable through the orifices 39 and 40 to engage the keyways 42 and 41, respectively, to secure the connector body 21 to the platform 20 and thereby the signal generator 10.

Referring now to FIG. 2, there shown a partial cutaway and cross section further illustrating the preferred embodiment of FIG. 1. In FIG. 2, the undersurface 22 of body 21 is resting on platform 20 of signal generator 10 with keys 43 positioned within keyways 41 and 42. Post 24 is shown in cross section to better illustrate the interaction of the key 43 within its keyway 42. In a preferred embodiment, the key 43 is wedge shaped such that its depth of insertion establishes the degree of urging of the body 21 toward the platform 20. That is, at a certain insertion depth, the upper surface of key 43 will engage the upper leading edge 45 of keyway 42. Insertion beyond this depth will increase the force exerted on edge 45 by the upper-surface of key 43 thereby increasing the force on the body 21 which urges the body 21 toward signal generator 10. Further, compression of the resilient washers by the shoulder 38 acts to maintain the forces interacting between the keyways 41 and 42, keys 43 and the orifices 39 and 40. For example, plastic has a tendency to distort or "cold flow" under pressure. The resiliency or elasticity of the washers 37 will assist in maintaining the forces initiated by insertion of the keys 43. It should be noted that this "cold flow" will result in a ridge forming behind the lower trailing edge 46 of the keys 41 and 43 if they are inserted such that the edge 46 is within the body 21. This ridge will act to hold the keys in position.

As described above, it is preferable if the keys 43 have a wedge shape. More preferably, the wedge shaped keys should have a "locking taper" which establishes forces of a nature which will tend to maintain the wedge in position, in known manner. With reference to FIG. 3, a locking taper exists if the angle A is seven degrees or less.

Obviously, many modifications and variations of the present invention are possible in light of the above teachings. For example, FIG. 4 illustrates a modification of the posts 23 and 24 of FIGS. 1 and 2. In FIG. 4, post 50 has any suitable cross section as may the post 23 and 24 of FIGS. 1 and 2, all posts herein being illustrated as circular and cross section. However, instead of the keyway taking the form of an aperture through the post, the keyway 51 is formed as a notch in the side of the post 50. Further, while the disclosed embodiments illustrates two post/wedge assemblies, other numbers of such assemblies may be employed or, alternatively, one or more such assemblies may be employed with other mechanical fasteners. Additionally, it is presently believed that when two fastening assemblies are employed, it is preferable that the orifices be orthogonal to each other and to the apertures that they intersect to maximize the constraints that they provide on movement of the body 21 relative to the platform 20. It is therefore to be understood that, within the scope of the appended claims, that the invention may be practiced otherwise than as specifically described.

What is claimed is:

1. In a body implantable signal generator assembly of the type having signal generator means having a surface, preformed connector means and mechanical securement means securing said connector means to the surface of said generator means, the improvement wherein said mechanical securement means comprises:

means extending from said signal generator means surface, said extending means including keyway means;

aperture means within said preformed connector means configured to accept said extending means;

orifice means angularly intersecting said aperture means; and key means inserted in said keyway means through said orifice means, said key means comprising wedge means for urging said connector means toward said generator means surface with the degree of urging being in accordance with the depth of insertion of said key means within said keyway means.

2. The signal generator of claim 1 wherein there are at least first and second extending means, aperture means and orifice means, said aperture means being generally parallel and said orifice means being non-parallel to each other and said aperture means.

3. The signal generator of claim 2 wherein said extending means comprises post means.

4. The signal generator of claim 3 wherein said post means are generally parallel to each other, said orifice means being generally orthogonal to each other and said post means.

5. The signal generator of claim 2 wherein said orifice means are generally orthogonal to each other and said aperture means.

6. The signal generator assembly of claim 1 wherein said wedge means comprises locking taper means.

7. The signal generator assembly of claim 6 wherein said keyway means comprises an aperture through said extending means.

8. The signal generator of claim 1 further comprising resilient means intermediate said signal generator means surface and said connector means, said resilient means being in compression with the degree of the compressing force being dependent on the depth of insertion of said key means.

9. The signal generator of claim 1 wherein there is at least one extending means, aperture means, orifice means and engaging means.

* * * * *